United States Patent
Van Pelt et al.

(10) Patent No.: US 12,118,724 B2
(45) Date of Patent: *Oct. 15, 2024

(54) INTERACTIVE CORONARY LABELING USING INTERVENTIONAL X-RAY IMAGES AND DEEP LEARNING

(71) Applicant: KONINKLIJKE PHILIPS N.V., Eindhoven (NL)

(72) Inventors: Roy Franciscus Petrus Van Pelt, Tilburg (NL); Javier Olivan Bescos, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/508,319

(22) Filed: Nov. 14, 2023

(65) Prior Publication Data

US 2024/0078676 A1 Mar. 7, 2024

Related U.S. Application Data

(63) Continuation of application No. 17/052,379, filed as application No. PCT/EP2019/060430 on Apr. 24, 2019, now Pat. No. 11,861,825.

(30) Foreign Application Priority Data

May 3, 2018 (EP) .................................. 18170529

(51) Int. Cl.
   *G06T 7/00* (2017.01)
   *G06T 11/60* (2006.01)
   (Continued)

(52) U.S. Cl.
   CPC ............ *G06T 7/0012* (2013.01); *G06T 11/60* (2013.01); *G16H 10/60* (2018.01); *G16H 30/40* (2018.01);
   (Continued)

(58) Field of Classification Search
   CPC .................. G06T 7/0012; G06T 11/60; G06T 2207/20081; G06T 2207/30101; G16H 10/60; G16H 30/40; G16H 50/50
   See application file for complete search history.

(56) References Cited

U.S. PATENT DOCUMENTS

| | | |
|---|---|---|
| 7,519,207 B2 | 4/2009 | Luo et al. |
| 2015/0254555 A1 | 9/2015 | Williams, Jr. et al. |

(Continued)

FOREIGN PATENT DOCUMENTS

| | | |
|---|---|---|
| CN | 107563123 A | 1/2018 |
| EP | 2942006 A1 | 11/2015 |

(Continued)

OTHER PUBLICATIONS

PCT/EP2019/060430 ISR & WO Jul. 8, 2019, 17 Page Document.
(Continued)

*Primary Examiner* — Casey L Kretzer

(57) ABSTRACT

A method for classifying a vasculature comprises training a training device with an initial model of a vasculature using diagnostic image data representing a geometry for a plurality of vessels of a vessel tree and including a respective vessel labeling for each vessel, providing at least one diagnostic image of a patient's vessel tree and identifying a variation between the vessel tree represented by the initial model and the patient's vessel tree. This variation is checked and labeled in order to improve the trained model. The process may be repeated iteratively until reaching an accurate patient-specific model of the vasculature.

20 Claims, 3 Drawing Sheets

(51) Int. Cl.
    *G16H 10/60* (2018.01)
    *G16H 30/40* (2018.01)
    *G16H 50/50* (2018.01)

(52) U.S. Cl.
    CPC ... *G16H 50/50* (2018.01); *G06T 2207/20081* (2013.01); *G06T 2207/30101* (2013.01)

(56) References Cited

U.S. PATENT DOCUMENTS

| | | |
|---|---|---|
| 2015/0265162 A1 | 9/2015 | Lavi et al. |
| 2016/0166209 A1 | 6/2016 | Itu et al. |
| 2016/0247279 A1 | 8/2016 | Lavi et al. |
| 2016/0364528 A1 | 12/2016 | Reicher et al. |

FOREIGN PATENT DOCUMENTS

| | | |
|---|---|---|
| JP | 03102477 U | 10/1991 |
| JP | 04125779 U | 11/1992 |
| JP | 04332548 A | 11/1992 |
| JP | 2008520344 A | 6/2008 |
| JP | 2018061771 A | 4/2018 |
| WO | 2015153362 A1 | 10/2015 |
| WO | 2017114700 A1 | 7/2017 |

OTHER PUBLICATIONS

Bai et al: "Semi-Supervised Learning for Network-Based Cardiac MR Image Segmentation"; MICCAI 2017, Part 11, LNCS 10434, pp. 253-260.

Hanneke et al: "Iterative Labeling for Semi-Supervised Learning"; Aug. 2010, University of Illinois, Dept. of Computer Science, 12 Page Document.

Nasr-Esfahani et al: "Segmentation of Vessels in Angiograms Using Convolutional Neural Networks"; Biomedical Signal Processing and Control, 40 (2018), pp. 240-251XCCCCCC.

INTERACTIVE CORONARY LABELING USING INTERVENTIONAL X-RAY IMAGES AND DEEP LEARNING

CROSS-REFERENCE TO RELATED APPLICATIONS

This application is a continuation application of U.S. application Ser. No. 17/052,379, filed on Nov. 2, 2020, which is a U.S. National Phase application under 35 U.S.C. § 371 of International Application No. PCT/EP2019/060430 filed Apr. 24, 2019, which claims the benefit of European Patent Application No. 18170529.4, filed on May 3, 2018. These applications are hereby incorporated by reference herein.

FIELD OF THE INVENTION

The present invention relates to a method for classifying a vasculature, a corresponding system and a respective computer program. In particular, the present invention relates to an improved method to train a training device to classify the vasculature with minimum user interaction, while at the same time keeping the size of the training dataset relatively small.

BACKGROUND OF THE INVENTION

Percutaneous coronary intervention (PCI) is a minimally-invasive procedure to treat narrowings, such as stenoses, of the coronary arteries as found in coronary artery disease. It is typically performed as an (X-ray) image guided therapy.

Image guidance for PCI usually includes visualization using respective diagnostic images. Prior to the PCI treatment, these diagnostic images allow to identify potential stenoses. After treatment, it is possible to assess the outcome of the treatment on the basis of the visualization.

The patient-specific (coronary) anatomy pre- and post-treatment as derived from the diagnostic images are typically stored, amongst further patient-specific information, in electronic medical records (EMR). The thus stored information is then used for case reports, for reference in the EMR and/or for interdisciplinary communication. Further, the information is provided to so-called registries which collect the disease-specific information in order to analyze it for statistical evaluation with respect to e.g. trends and treatments for a specific disease.

In order to establish a smooth and lean storing and exchange process for this information, it has to be ensured that the information provided to the different entities is unambiguous and easy to interpret. This typically requires a pre-determined format/structuring of the information according to known medical terminology and coding standards, such as the "Systematized Nomenclature of Medicine" (SNOMED) CT.

In PCI, the documenting of the patient-specific pre- and post-treatment information relating to the intervention is based on the patient-specific coronary vasculature, either by annotating the collected images, by creating a customized schematic representation or by providing a textual documentation. Out of these options, the employment of a customized schematic representation is generally considered the preferable way to communicate the course of the intervention. However, generating such a customized schematic for each patient individually is a very time-consuming process and requires an extensive amount of manual work (input, replication, or the like) by the physician.

SUMMARY OF THE INVENTION

In order to reduce the manual work to be done by the physician, efforts have been made to find procedures that allow to automatically detect and label the vessels in the patient's vasculature. These approaches facilitate direct structured reporting with minimal involvement of the physician. The underlying principles of these approaches typically involve the extraction of centerlines, e.g. by means of morphological image processing operators. The thus extracted centerlines are considered as representing the geometry, including length, course, etc., of the different vessels in the (coronary) vasculature. They are matched against a standard model of a vasculature and, based on said matching, the labeling is performed.

However, there is a huge morphological variation in the coronary vasculature in different patients. That is, the geometry of the vessels for each patient is different, in that the length, course, direction or the like of the vessels, and, thus, the topological structure of the vessel tree, may differ from patient to patient. Thus, the use of a standard model for a vasculature representing a "typical" vessel topology only has limited accuracy which is particularly not sufficient for clinical practice.

It is therefore an object of the present invention to provide an improved method and corresponding system for classifying a patient's vasculature. It is a further object of the invention to provide an improved method for classifying a patient's vasculature which allows to improve the accuracy of the detection and subsequent labeling of the vessels in a vasculature on the one hand but avoids unnecessary manual work for the physician on the other. More particularly, it is an object of the invention to provide a method for training a training device to perform the automatic detection and labeling with a small training dataset.

Thus, a method is provided for classifying a vasculature, the method comprising the steps of: a) training a training device with an initial model of the vasculature using diagnostic image data representing a first vessel tree, said diagnostic image data comprising a corresponding vessel labeling for at least one vessel of said first vessel tree, b) inputting at least one diagnostic image representing a second vessel tree, c) identifying at least one deviation between the first vessel tree and the second vessel tree, d) in response to the identifying, outputting an indication of said at least one deviation to a user and providing at least one labeling for said at least one deviation, and e) adjusting, based on the at least one deviation and the at least one labeling, the initial model to classify the vasculature.

In accordance with this method, it is possible to train a training device to automatically detect and label the individual vessels in a patient's vasculature using only a small (initial) training dataset. The training device may particularly implement a deep learning algorithm to derive, from the training dataset, an association between a particular vessel of the vasculature and its corresponding label.

In this context, the term diagnostic image data may particularly refer to one or more images representing a patient's vasculature, in particular a patient's coronary vasculature. The diagnostic images may be acquired using any medical imaging modality suitable for imaging a vasculature. In some specific embodiments, the diagnostic images used for the initial training dataset may particularly be obtained using an X-ray imaging modality. In other embodiments, the diagnostic images may also be obtained using a different imaging modality, such as magnetic resonance imaging, ultrasound imaging or the like. In some embodiments, the plurality of diagnostic images in the diagnostic image data may particularly comprise temporal sequences of the patient's vasculature, i.e. may correspond to a movie of the patient's vasculature captured over a certain time.

The term initial model of a patient's vasculature may particularly refer to a trained model of the patient's vasculature which has been taught to the training device using a set of diagnostic image data acquired for a plurality of patients. In this context, the set of diagnostic image data should be a comparatively small set of diagnostic image data compared to prior art approaches.

That is, the training device may initially be trained with diagnostic image data comprising multiple images or image sequences which have been acquired for a plurality of different patient as a training dataset. Using multiple images or multiple image sequences for different patients allows to capture a variety of anatomical structures. The image sequences may particularly be temporal sequences. By using all frames from the (temporal) sequence of images that show the vessel tree a large training dataset may be provided which allows for free data augmentation.

Hereby, the size of the training dataset should hereby be selected as large as necessary, but as small as possible, in order to achieve a training of the training device with a sufficiently reasonable first classification of the vessels. The resulting initial model, while not (yet) being all-encompassing, thus sufficiently represents the different possible geometries of the vessel tree (i.e. the geometry of one or more of the vessels of said vessel tree) that may be found in different patients.

Hereby, the training may particularly be performed by identifying the vessel trees indicated in the diagnostic image data set including the diagnostic images. To that end, in these diagnostic images, a vessel tree comprising one or more, in particular a plurality of, vessels may be visible. Hereby, it shall be understood that the term vessel tree may refer to one or more vessels that form the patient's vasculature or a part thereof.

Further, the term geometry of the vessel tree may refer to the geometric properties, i.e. the course, length, etc., of each of the vessels identified in the vessel tree. Alternatively, the term geometry may refer to the course, length, etc. of a subset of the plurality of vessels in the vessel tree. In some embodiments, the term geometry may also refer to the geometry of only a single vessel in the vessel tree. The term geometry may also be referred to as vessel geometry.

To that end, the geometry of the plurality of vessels in the vessel tree may further allow to determine the vessel topology, i.e. structural relationship between individual vessels in the vasculature.

In order to identify the vessels, the diagnostic image data may further comprise a respective vessel labeling for at least one, more particularly for a subset or each of, the vessels in the vessel tree. That is, the diagnostic image data comprises at least one, and in particular a plurality of, vessel labelings that corresponds to the vessels represented by the diagnostic images, whereby each vessel labeling may be provided to one particular vessel.

In order to obtain such vessel labeling, the geometry of the vessels may particularly be determined using a centerline extraction approach, in which the centerlines of each vessel are identified and locally refined as described e.g. in U.S. Pat. No. 9,129,417 B2. These centerlines allow to determine the geometry of the vessels in the vasculature. The thus identified geometry of the vessel tree may then be (manually) labeled with respective vessel labelings for the vessels represented therein.

It shall be understood that the vessel labeling shall particularly be provided for each vessel represented by the initial model or for a subset thereof. Hereby, the vessel labeling may particularly be provided at least for vessels that are that is considered to form part of a standard anatomical model, i.e. for the vessels of the vasculature that are most common in all patients. By identifying the most common vessels it is possible to obtain the highest diagnostic insight into the model. In case of the coronary vasculature, these most common vessels may particularly concern vessels such as the left coronary artery (LCA) with the left anterior descending artery (LAD) and the circumflex (CX), the right coronary artery with the posterior descending artery (PDA) and the like. Once these vessels are labeled, the labeling may be continued for $2^{nd}$ and $3^{rd}$ order branches as well, if necessary. This ensures a high accuracy of the training of the patient-specific initial model and, since this initial model corresponds to the starting point for the further training steps of the subsequent learning of the training device. The vessel labeling may particularly be performed manually by a user, such as a physician.

Upon training the training device with the patient-specific initial model using the diagnostic image data obtained for said patient, at least one (further) diagnostic image acquired for the patient may be input. The at least one diagnostic image may particularly have been obtained using the same imaging modality of used for the plurality of images of the diagnostic image data.

The at least one diagnostic image may represent a second vessel tree and may also allow to determine to the geometry of one or more vessels of said second vessel tree. In order to properly derive this (second) geometry of vessels, a centerline extraction approach as mentioned herein above may be performed on the at least one diagnostic image. In that context, the at least one diagnostic image may particularly be input along with the centerlines that have been extracted therefrom. The at least one diagnostic image may hereby particularly be provided to an input unit. The input unit may be a part of the training device. Alternatively, the input unit may be communicatively coupled to the training device.

Upon identification of the geometry of the vessels in the at least one diagnostic image, i.e. upon identification of the second vessel tree, the first vessel tree and the second vessel tree may be compared to one another.

That is, it may be identified whether a vessel that is part of the first vessel tree may also be found in the second vessel tree and whether said vessel of the second vessel tree corresponds, in terms of geometry, i.e. in terms of length, course, position, direction, etc. to the corresponding vessel of the first vessel tree. This allows to identify the geometric and/or topological differences—or deviations or variations—between the first vessel tree as represented by the initial model and the second vessel tree as determined from the at least one diagnostic image.

These deviations may particularly relate to anatomical variations: In some embodiments, a vessel may be present in the second vessel tree but may not be present in the first vessel tree. This additional vessel may then be identified as a deviation between the first and the second vessel tree. This additional vessel present in the second vessel tree may typically not have any vessel labeling yet. The labeling may accordingly have to be added to update the initial model.

In some embodiments, a vessel that is present in the first vessel tree may be missing in the second vessel tree. The initial model may thus be updated in that that particular vessel may be removed.

In some embodiments, the deviation may also correspond to a difference in geometry between corresponding vessels in the first and second vessel tree. That is, the corresponding vessels may differ in terms of length, course, position, direction, or the like. This variation in terms of length, course, position, direction etc. may thus also be trained to the initial model in order to update this model.

A difference in geometry may hereby particularly be determined by obtaining a difference value and comparing said difference value to a predetermined threshold. If the difference value does not exceed the threshold value, no deviation is identified. In case the threshold value is exceeded, a deviation is present and an indication of said deviation is output to a user. Further, a labeling for the concerned vessel or vessels is provided.

Thresholding may hereby be performed on different levels. In one level, the first vessel topology of the first vessel tree and the second vessel topology of the second vessel tree may be determined. The first vessel topology and the second vessel topology may be compared with one another in order to identify deviations between the first vessel topology and the second vessel topology. These deviations may then be identified using one or more difference values in order to determine whether they are due to measurement and/or imaging errors or due to actual geometric and/or topological deviations between the first and second vessel tree. In another level, one may use pixel data to determine the deviations. That is, a training on pixel data may be performed. Then, one or more pixels may receive a confidence that they belong to a particular vessel (e.g. LCA or LAD). Subsequently, the received confidence may be thresholded and may help to identify whether there are vessels missing in the first and/or second vessel tree compared to the second and/or first vessel tree. This allows to identify missing and/or additional vessels.

Subsequently, a labeling may be provided for the deviation in the at least one diagnostic image. That is, a vessel that is present in the second vessel tree but not in the first vessel tree may be labeled with a corresponding labeling. Additionally or alternatively, a vessel having a different length, course or the like in the second vessel tree than in the first vessel tree may be labeled with its corresponding vessel labeling, such as to identify the deviation of the topology in that respect in the at least one diagnostic image.

In that context, it shall be understood that indicating to a user may comprise a suggestion to a user as to how to label and/or treat the respective deviation. Alternatively, the indication may be a request to a user to label and/or treat the deviation manually based on experience. This indication may particularly be a visual indication, but may also be haptic or auditory.

The at least one diagnostic image may thus be provided with a respective labeling of one or more vessels in the second vessel tree. Subsequently, the at least one diagnostic image is used, along with the newly added labeling as corresponding vessel annotation, to adjust the patient-specific initial model of the vasculature.

In that context, the term adjusting may particularly refer to changing or updating the initial model in accordance with the new information provided. This changing may particularly be performed by implementing a semi-supervised learning approach in the training device. Additionally or alternatively, the changing may be performed by adding, upon labeling, the at least one diagnostic image to the diagnostic image data and retraining the training device using the thus updated training dataset.

In accordance with this approach, rather than using an all-embracing training dataset from the beginning, the training device is trained with an initial model of the vasculature using a relatively small training data set constituted by the diagnostic image data as a starting point and subsequently only trained by deviation from said initial model using the identified deviations, which correspond to variations in the vessel topology in the vasculature of different patients, i.e. differences found between the vessels of the first vessel tree (as represented by the initial model) and the second vessel tree (as derivable from that at least one image). Thereby, patient-specific anatomical variations are gradually introduced into the initial model. This allows to improve the accuracy of the model of the vasculature by individualizing it for one particular patient while at the same time keeping the initial training dataset rather small.

In some embodiments, the providing the at least one labeling comprises a receiving a first user input from said user indicating said at least one labeling.

In some embodiments, the labeling of the deviation, in particular the labeling of the yet unidentified vessels represented by the at least one diagnostic image, may be performed using an interactive approach with a user. That is, the user may be presented with the deviation and requested to manually input a labeling for said deviation. In case the deviation corresponds to one or more additional vessels, the user may particularly manually label the one or more additional vessels. If the deviation corresponds to a difference in geometry, i.e. a different course, length, position, direction, or the like, of a previously labeled vessel, the user may be requested to either confirm that the vessel labeling is correct or to input a new vessel labeling. This allows to update the overall topology of the vasculature in accordance with the patient-specific data.

In some embodiments, the adjusting the initial model to classify the vasculature comprises iteratively repeating steps b) to e) for a plurality of diagnostic images. By means of iteratively repeating the steps of inputting at least one diagnostic image acquired from a patient, identifying the deviations between the first vessel tree according to the initial model with the second vessel tree obtained from at least one diagnostic image acquired for the patient, providing a labeling for the deviations/variations identified between the first and second vessel tree and adjusting the initial model accordingly, the training dataset may be gradually expanded.

This gradually improves the accuracy of the trained model of the vasculature for a particular patient. As a result, the amount of deviations/variations identified between the initial (i.e. the gradually trained) model and the patient-specific vasculature will gradually decrease, as the initial model approaches the patient-specific actual vasculature. This allows to introduce only as many images into the training dataset for training the training device as necessary until reaching an accurate model of the patient's vasculature, thereby decreasing the amount of input data necessary, while at the same time keeping the necessary user input at minimum, as the user is only asked to provide input upon identification of a deviation/variation.

In some embodiments, the adjusting the initial model comprises retraining said training device using said diagnostic image data representing said first vessel tree along with the at least one diagnostic image representing the second vessel tree and the corresponding at least one labeling.

In some embodiments, the adjusting of the initial model of the vasculature may particularly be performed by retraining the training device with an updated training dataset comprising the initially used diagnostic image data and the additional at least one diagnostic image of the patient's vasculature including the identified vessels and the corresponding labeling. That is, upon labeling of the vessels identified in the at least one diagnostic image, said diagnostic image may be added to the training dataset. Upon retraining, the initial model the training device has been trained with may more closely resemble the patient-specific vasculature of the patient for whom the at least one diagnostic image has been obtained. Thereby, the trained initial model is gradually adjusted to accurately represent the patient-specific vasculature.

In some embodiments, the method further comprises identifying a geometry of the second vessel tree in the at least one diagnostic image by segmenting the at least one diagnostic image, identifying, based on said segmenting, respective centerline information for a plurality of vessels of said second vessel tree and extracting said centerline information. In some embodiments said centerline information is input along with the at least one diagnostic image.

In some embodiments, the geometry of the second vessel tree that is represented by the at least one diagnostic image may particularly be determined using a centerline extraction approach as mentioned herein above. That is, the at least one diagnostic image may be received and segmented. Based on said segmenting, the assumed geometry of the vessels in the vasculature imaged in the at least one diagnostic image may be predicted by providing an initial estimate of the centerlines through the vessels and subsequently refining said centerlines. The refined centerline information may then be considered as indicating the geometry of the vessels.

In some embodiments, the thus extracted centerline information is used, along with the at least one diagnostic image it has been extracted from, to adjust the initial model trained to the training device. That is, the at least one diagnostic image and the extracted centerline information are input into the training device, such that the training device may use this additional information to update the initial model accordingly. This allows for iteratively training the training device by techniques such as semi-supervised learning or by retraining upon adding the at least one diagnostic image and the corresponding labeling to the training dataset.

According to some embodiments, the deviation may comprise a variation between a geometry of the first vessel tree and a geometry of the second vessel tree, i.e. a geometric variation between the first and second vessel tree.

As indicated herein above, the deviation between the geometry of the first vessel tree as represented by the initial model and the geometry of the second vessel tree may be caused by geometric variations in the vessel tree which may result in topological variations of the vessel topology. Such a geometric variation may particularly correspond to an anatomical variation, such as missing vessels, missing branches, longer and/or shorter branches, highly tortuous branches or the like. Further, the course and/or direction and/or position of a particular vessel may differ from that of the corresponding vessel in the initial model or like variations may occur.

In some embodiments, the diagnostic image data comprises a plurality of images, in particular between 10000 and 100 images, even more particularly between 1000 and 100 images.

According to some embodiments, the diagnostic image data constituting the initial training dataset comprises a plurality of images, such as diagnostic images that have been obtained using a diagnostic imaging modality. Due to the iterative approach for training the training device, only a small initial training dataset is necessary. In some embodiments, between 1000 to 100, more specifically between 500 to 200 images are sufficient to train the training device with the initial model. Further deviations/anatomical variations specific to a certain patient may then gradually be introduced by means of the diagnostic images acquired for said patient which have been labeled through user interaction based on expert input.

In some embodiments, the training device is further trained to include externally-caused variations into the initial model.

In some embodiments, external factors may influence the diagnostic image data and/or the at least one diagnostic image. Examples of such external factors may relate to acquisition errors and/or measurements inaccuracies, such as a rather small and/or incomplete field of view or other disturbances which may negatively influence the acquisition accuracy of the imaging modality. Further, image acquisition may be negatively affected by devices that have been introduced into the patient such as stents, catheters, clamps or the like. Devices such as stents may also change the shape and/or course or the like of a particular vessel in the vasculature.

In order to take account for these external influencing factors, the variations resulting therefrom may be trained to the training device such as to be included in the initial model, thereby further improving the accuracy of the classification.

According to a further aspect, a classification system for classifying a vasculature is provided, the classification system comprising: a training device configured to be trained with an initial model of the vasculature using diagnostic image data representing a first vessel tree, said diagnostic image data comprising a corresponding vessel labeling for each vessel of said first vessel tree, an input unit configured to receive at least one diagnostic image representing a second vessel tree, and an inference unit configured to identify at least one deviation between the first vessel tree and the second vessel tree, to output, in response to the identifying, an indication of said at least one deviation to a user, and to provide at least one labeling for said at least one deviation, wherein the training device is configured to adjust, based on the at least one deviation and the at least one labeling, the initial model to classify the vasculature. In some embodiments, the classification system further comprises a display unit configured to display said indication of said at least one deviation to a user and a user interface configured to receive a first user input from said user indicating said at least one labeling.

In a further aspect, a classification system is provided which comprises a training device which may be trained with the initial model of the first vessel tree, an input unit which may receive the at least one diagnostic image representing the second vessel tree and an inference unit that may derive the deviation between the first and second vessel tree and output such deviation to a user. The inference unit may further provide at least one labeling for said deviation. In this context, the inference unit may particularly determine a potential labeling for a particular deviation and suggest said potential labeling to a user using a respective indication. Alternatively or additionally, the inference unit may be configured to use the indication to request the user to manually input a labeling. In some embodiments, the inference unit may also be configured to provide a list, which may be ranked or alphabetically sorted with suggested labelings to the user and have the user optionally select from said list or manually input a label.

Hereby, the system may particularly comprise a display unit or be communicatively connected to a display unit for displaying the indication to the user. Alternatively or additionally, the system may also comprise an additional or integrated indication unit which provides an auditory and/or haptic indication to a user to prompt the user to interact with the classification system.

The classification system may particularly comprise a user interface to receive user input. The user input may particularly be used to input the labeling of the one or more deviations between the first and second vessel tree. Further, the user input may be used to obtain additional information, such as time, imaging conditions, or the like. The user interface may particularly comprise a keyboard, a mouse and/or the like. In some embodiments, the user interface may be provided as part of the display unit, e.g. in terms of a touchscreen. Alternatively, the user interface may be a touchscreen provided in addition to the display unit. In some embodiments, the user interface may be provided as a combination of several interfaces, such as a combination of a touchscreen, a keyboard and/or a mouse or the like. Further user interfaces may be imagined, as long as they allow a user to interact with the classification system.

In some embodiments, the inference unit is further configured to generate a medical representation, the representation comprising at least the vasculature, i.e. the vessels as that have been identified for the patient, the vessel labeling and the at least one labeling, and to transmit said representation to a database. In some embodiments, the database comprises an electronic medical record (EMR), and the medical representation is generated according to a predetermined format of the electronic medical record.

In some embodiments, the inference unit may generate a medical representation from the diagnostic image data, the at least one diagnostic image and the corresponding labeling of the at least one diagnostic image. In some embodiments, the medical representation may also be generated elsewhere, for example by a dedicated generation unit. In that context, the term medical representation may particularly refer to a customized schematic representation which allows to communicate the course of the intervention that may be performed on the patient to third parties not directly involved with said intervention. Alternatively or additionally, the term medical representation may also encompass a graphical representation, in particular a three-dimensional representation, of the model of the patient's vasculature. In some embodiments, the graphical representation may also include the vessel labeling for all vessels shown in the model of the patient's vasculature. In some embodiments, the graphical representation may be displayed on the display unit. During display, the vessel labeling may be switched on or off, moved, changed in appearance or the like, by the user.

The medical representation, in particular the customized schematic representation of the vasculature, may be transmitted and stored in a corresponding (medical) database for further analysis of trends and treatments, for communication with other physicians, case reports or the like. In some embodiments, the medical representation is generated according to a pre-defined format, such as SNOMED CT. This generation may particularly be performed automatically, based on the model trained to the training device. By automatically generating of a patient-specific medical representation that complies with the strict data structure imposed on the data by third parties, such as a registries or organizations that collect such information for trend analysis, direct structure reporting with minimal user interference may be established.

In a further aspect, a computer program is provided which, when executed by a processing unit, is adapted to perform the method according to the invention. In an even further aspect, a computer-readable medium having stored thereon the computer program is provided.

It shall be understood that the classification system for classifying a vasculature may be implemented by means of a processing unit. Hereby, the training device, the input unit and the inference unit may be implemented as modules in the processing unit. The functionality of these modules may in particular be implemented by means of a respective algorithm.

It shall be understood that the classification method of claim 1, the classification system of claim 10, the computer program of claim 14, and the computer-readable medium of claim 15, have similar and/or identical preferred embodiments, in particular, as defined in the dependent claims.

It shall be understood that a preferred embodiment can also be any combination of the dependent claims or above embodiments with the respective independent claim.

These and other aspects will be apparent from and elucidated with reference to the embodiments described hereinafter.

DETAILED DESCRIPTION OF EMBODIMENTS

Figure 1:
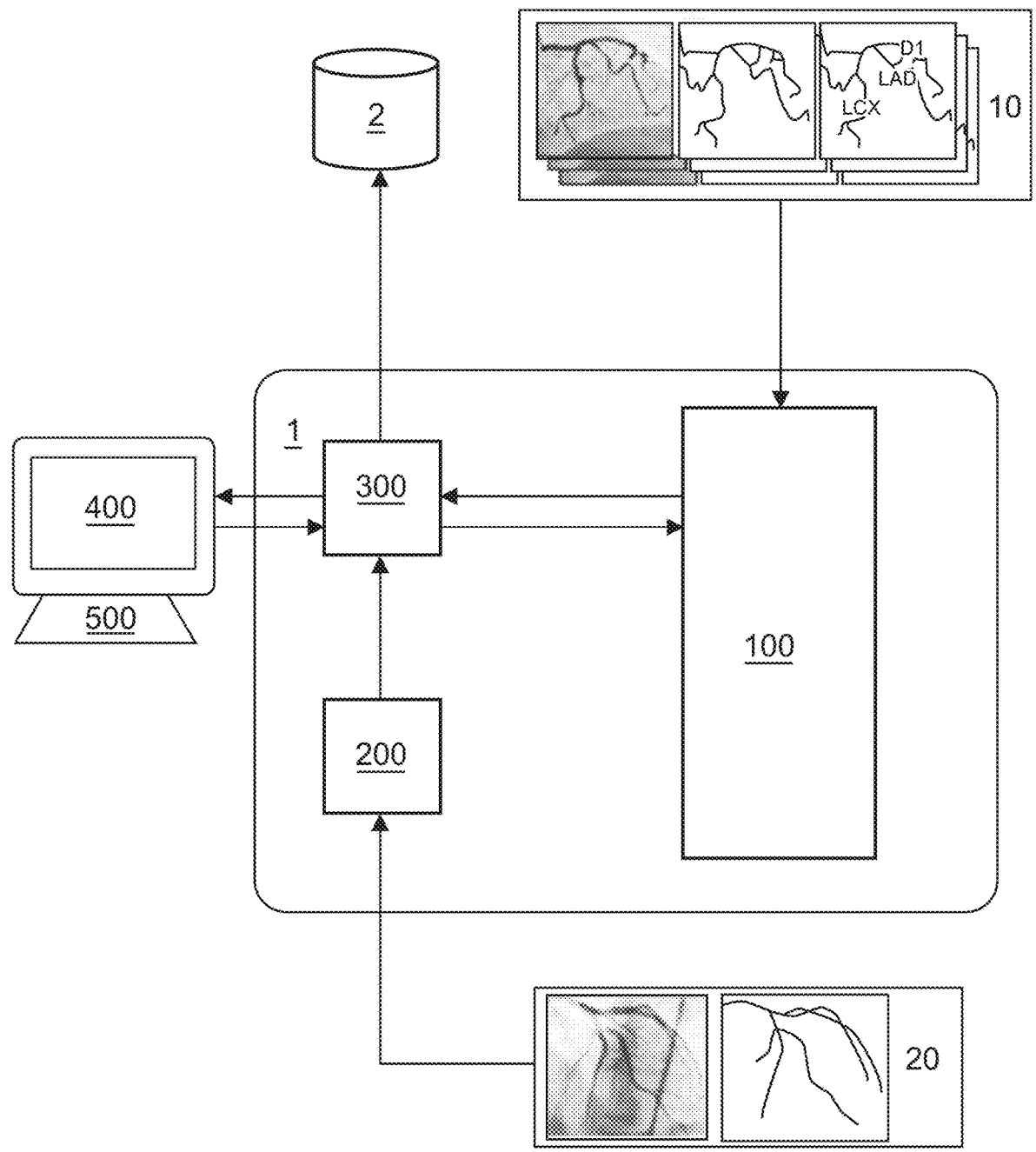
FIG. 1 schematically illustrates a classification system for classifying a patient's vasculature according to an embodiment.

The illustration in the drawings is schematically. In different drawings, similar or identical elements are provided with the same reference numerals.

FIG. 1 shows a schematic illustration of a classification system 1 for classifying a patient's vasculature. In the exemplary embodiment of FIG. 1, the classification system 1 comprises a training device 100, an input unit 200, an inference unit 300, a display unit 400 and a user interface 500. Further, the classification system 1 is communicatively coupled to a database 2.

In the embodiment according to FIG. 1, the classification system 1 includes training device 100 which receives diagnostic image data 10 representing a first vessel tree. The training device 100 implements a deep learning algorithm which is trained using the diagnostic image data 10 as a training dataset. For that purpose, the diagnostic image data may particularly comprise about hundreds to thousands diagnostic images of the vasculature of multiple patients.

These are used to generate an initial model representing the vessels in the first vessel tree. In the exemplary embodiment of FIG. 1, the diagnostic images comprised in the diagnostic image data have been acquired using X-ray imaging. Other imaging modalities may, however, likewise be used as long as they enable an imaging of the vessels. Further, the diagnostic image data comprises a vessel labeling for one or more vessels, in particular for at least the vessels of a standard anatomical model of a vasculature. Using the diagnostic image data, the training device may then be trained, by a relatively small training dataset, with an initial model of a vasculature which includes the vessels of the first vessel tree.

The classification system 1 further comprises input unit 200. Input unit 200 is configured to receive a diagnostic image 20 representing a second vessel tree. The diagnostic image 20 has been acquired for the patient whose vasculature is to be assessed using the classification system. In the exemplary embodiment of FIG. 1, the at least one diagnostic image 20 has been obtained using X-ray imaging. Other imaging modalities, such as ultrasound imaging may likewise be used as long as they allow to identify the vessels in the patient's vasculature. In some embodiments, the diagnostic image 20 has been preprocessed elsewhere and the input unit 200 further receives the extracted centerline information for the second vessel tree, such as to allow for identifying its geometry and topology, along with the at least one diagnostic image. In some embodiments, the input unit 200 only receives the diagnostic image 20 and provides the diagnostic image 20 to inference unit 300 which then performs centerline extraction to identify the geometry of the vessels in the second vessel tree.

In the embodiment of FIG. 1, inference unit 300 thus receives the diagnostic image 20 representative of the second vessel tree from input unit 200 and, further, the initial model representative of the first vessel tree from training device 100. Inference unit 300 compares the first and second vessel tree with one another and identifies one or more deviations between the first and second vessel tree. To that end, inference unit 300 may particularly employ a difference approach, i.e. may obtain a difference for a particular variation between the geometries of the vessels in the first and second vessel tree, respectively, and comparing said difference value to a predetermined threshold. If the difference value is below said threshold, the difference is considered to be within the error range of the imaging modality and no deviation is identified. If the threshold value is exceeded, however, it is assumed that a deviation is present.

In case the inference unit 300 determines that a deviation is present, the inference unit 300 provides a respective indication to display unit 400. In the particular embodiment of FIG. 1, display unit 400 comprises a computer screen, on which a visual indication that a deviation has been detected may be displayed to a user. Accordingly, display unit 400 may generate said visual indication. The display unit may 400 particularly provide a graphical representation of some or all of the vessels in the second vessel tree along with a marker or other indicator to indicate the deviation identified. The display unit 400 may further output a request to a user to provide a labeling for the deviation. This request may either be a suggestion as to how to label the deviation, which the user simply has to accept or decline, or a list of possible labeling suggestions of which the user shall select. The request may also be an indication to manually input a label for said deviation. Further requests may also be envisioned that prompt the user to interact with the system 1.

The user may particularly provide a respective user input indicating the labeling via user interface 500. In the exemplary embodiment of FIG. 1, user interface 500 may particularly comprise a keyboard. Further, user interface 500 may comprise a touchscreen, a mouse, a remote control or the like.

Once the user has input the labeling, the thus labeled diagnostic image 20 is then returned to inference unit 300 which transmits the diagnostic image 20, along with the labeling input by the user, to training device 100 to expand the training set for training device 100 by said diagnostic image 20 and the labeling. Based on the thus expanded training set, training device 100 may then use the diagnostic image 20 and the labeling to adjust the (initial) model of the vasculature accordingly. It shall be understood that the adjusting of the model may be performed in a number of ways, e.g. by semi-supervised learning or by adding the labeled diagnostic image 20 to the diagnostic image data 10 and retraining the training device. In the specific embodiment according to FIG. 1, the training device is retrained with a new model based on an updated training dataset including the newly labeled diagnostic image 20.

According to the embodiment of FIG. 1, the process is iteratively repeated for a plurality of diagnostic images 20 that have been acquired for the patient. Each diagnostic image 20 is hereby processed and labeled as described above and subsequently used to retrain the training device. By means of this iterative retraining, the model that is trained to the training device is gradually adjusted to approach the vasculature of the patient for whom the diagnostic images are collected. Thus, while at the beginning of the process the user interactions will be manifold, as many deviations may be identified, the required user input will diminish over time as the trained model resembles the patient-specific vasculature more and more closely. By means of this approach, an accurate automatic labeling of the vessels in the vasculature may gradually be achieved that also takes account of the anatomical variations for each patient.

By means of this automatic labeling approach, a medical representation, particularly a customized schematic representation of the patient's vasculature, may be obtained. This medical representation may be structured according to a predetermined format. In the particular embodiment according to FIG. 1, the medical representation may particularly be structured according to the medical terminology and coding standard that is required according to SNOMED CT.

The thus structured data may then be transmitted to and stored in database 2. Database 2 may be accessed by other physicians to obtain patient information and case reports and/or by third parties, such as registries or organizations for treatment and trend analysis and prognosis. Since the medical representation is provided in a pre-determined format, the information provided therein may be interpreted easily and in an unambiguous manner.

Figure 2:
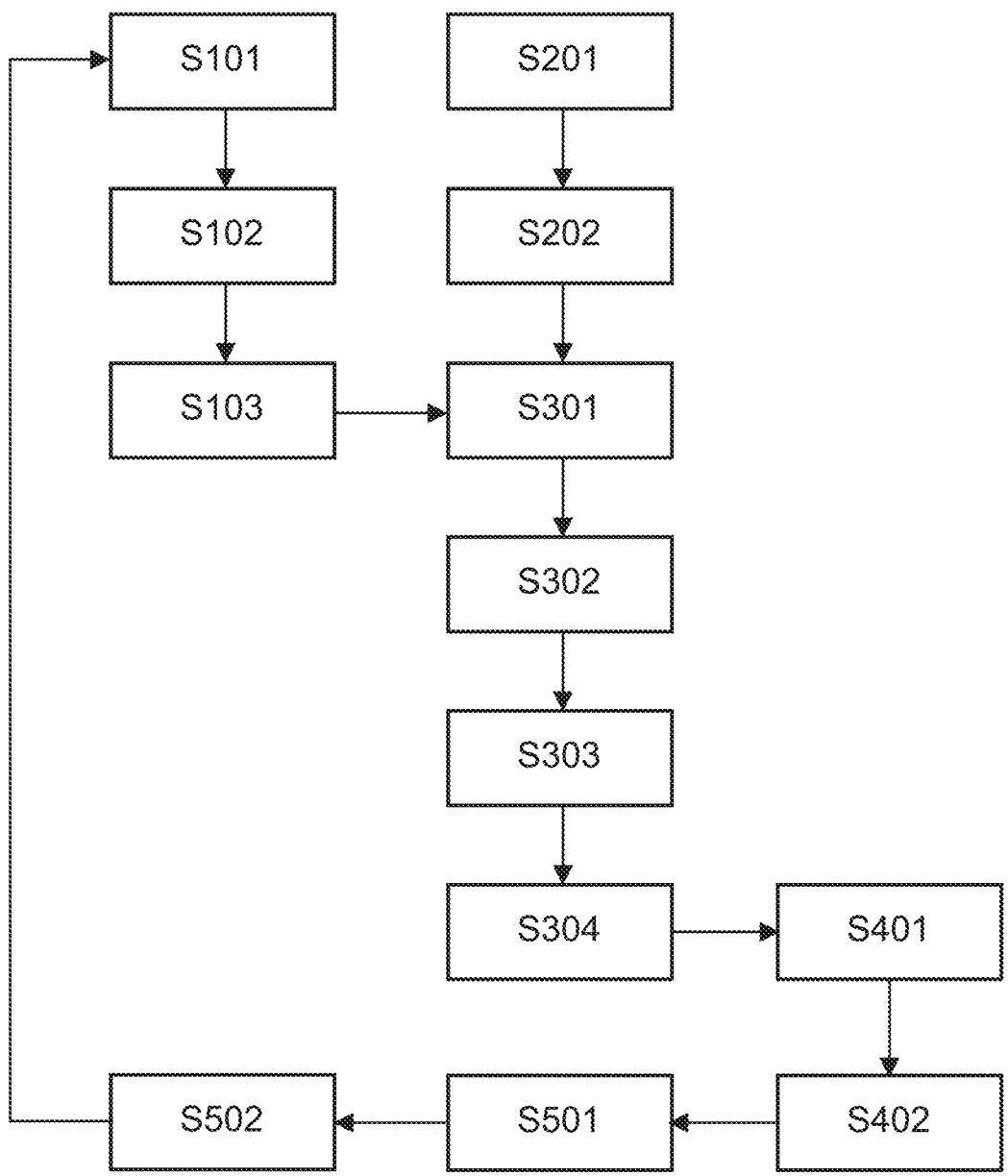
FIG. 2 illustrates a method for classifying a vasculature according to an embodiment.

FIG. 2 schematically illustrates a method for classifying a patient's vasculature according to an embodiment. In step S101, the training device 100 receives the diagnostic image data 10 representing a first vessel tree. In step S102, the training device 100, implementing a deep learning algorithm, is trained using the diagnostic image data 10 as a training dataset. The diagnostic image data may hereby particularly comprise hundreds to a thousand diagnostic images of multiple patients representing a plurality of vessels and a corresponding vessel labeling for at least a subset of these vessels. In step S103, the initial model that has been trained using the diagnostic image data 10, which represents the first vessel tree including the vessel labeling, is provided to inference unit 300.

In step S201, input unit 200 receives a diagnostic image 20 acquired from a patient representing a second vessel tree. In the exemplary embodiment of FIG. 2, the input unit 200, in step S202, provides the diagnostic image 20 to inference unit 300 for further processing. In this context, it may be understood that, in alternative embodiments, the diagnostic image 20 received by input unit 200 may be preprocessed and may thus comprise extracted centerline information which is then passed, along with the diagnostic image 20, to inference unit 300.

In step S301, inference unit 300 receives the diagnostic image data 20 representative of the second vessel tree from input unit 200. Further, also in step S301, inference unit 300 receives the initial model representative of the first vessel tree from training device 100. In step S302, inference unit 300 identifies the geometry of the vessels in the second vessel tree represented by the diagnostic image 20 received from input unit 200. In the exemplary embodiment of FIG. 2, inference unit 300 particularly uses a centerline extraction approach to identify the geometry of the vessels. In step S303, inference unit 300 then compares the first and second vessel tree, in particular their respective geometries, with one another and identifies one or more deviations between them, e.g. by means of the above-described difference approach.

When a deviation is found by inference unit 300, inference unit 300, in step S304, provides a respective indication to display unit 400. In step S401, the indication is received by display unit 400 which presents this indication, in step S402, to a user. In the embodiment according to FIG. 2, the indication provided to the user may particularly be a visual indication. The indication may further comprise a haptic and/or auditory component. To that end, display unit 400 may optionally generate, in step S402, a graphical representation of the vessels in the second vessel tree along with a marker or other indicator to indicate the identified deviation and output a request to a user to label said deviation by means of the user interface 500.

In step S501, the indication is output to a user to prompt the user to provide, via the user interface, a respective interactive input for labeling the deviation. In step S502, the user may optionally manually label the deviation in response to the request by the system.

In the particular embodiment according to FIG. 2, the user input providing the respective labeling prompts the system to return to initial training step S102. That is, the at least one newly labeled diagnostic image 20 is input into training device 100 which then adjusts the initial model in accordance with the new labeling. In the exemplary embodiment of FIG. 2, this is achieved by adding the newly labeled diagnostic image to the diagnostic image data in order to expand the training dataset and retraining the training device with the expanded training dataset.

These steps may be iteratively repeated for a plurality of diagnostic images that have been acquired for the patient. By means of this iterative retraining, the model that is trained to the training device is gradually adjusted to approach the patient-specific vasculature. This leads to a gradual reduction of necessary user interactions while at the same time keeping the used training dataset as small as possible.

Figure 3:
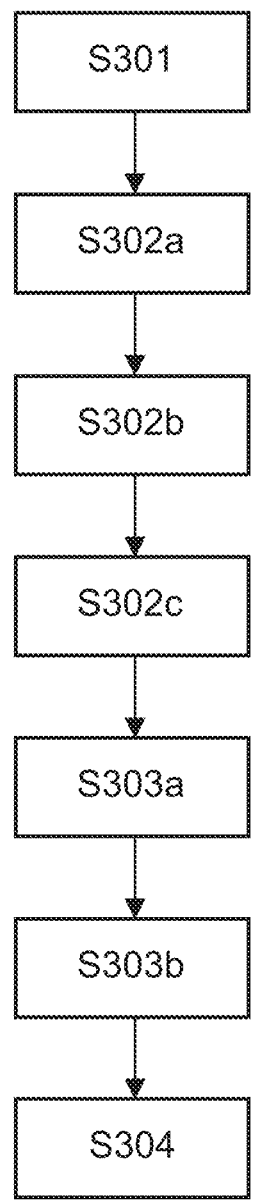
FIG. 3 schematically illustrates a detailed method for identifying a geometry of a second vessel tree from at least one diagnostic image and for identifying a (geometric) variation between said second vessel tree and a first vessel tree according to an embodiment.

FIG. 3 schematically illustrates a detailed method for identifying the geometry of the vessels in the second vessel tree from at least one diagnostic image and a deviation in geometry between the vessels of said second vessel tree and the vessels of the first vessel tree according to an embodiment.

Specifically, in step S301, the initial model as provided by the training device 100 and the diagnostic image 20 as provided by the input unit 200 are received at the inference unit 300. In step S302a, the inference unit segments the diagnostic image 20 and, in step S302b extracts, based on the segmentation, the centerlines according to a known centerline extraction approach. Based on these extracted centerlines, the inference unit, in step S302c, identifies the geometry of the vessels in the second vessel tree. In step S303a, the inference unit 300 then compares the geometry of the vessels in the first vessel tree as inferred from the trained initial model with the geometry of the vessels in the second vessel tree as identified from the diagnostic image 20. The comparison may particularly be performed by determining a difference value for selected points in the vessels in the first and second vessel tree, respectively, and comparing the difference value to a respective threshold in order to determine whether the difference is due to inaccuracies or due to actual geometric (and, thus, anatomical) variations between the vessels of the first and second vessel tree.

Based on this comparison, the inference unit, in step S303b, identifies at least one deviation, such as a geometric or topological variation, between the vessels of the first and second vessel tree. In step S304, the inference unit 300 indicates the one or more identified deviations to display unit 400 for indicating the deviations to the user and prompting the user to interact with the data. This allows to interactively expand the data set used to define the model of the patient's vasculature, gradually improving the models accuracy and allowing for a more and more autonomous labeling and structure reporting with improved accuracy, while maintaining the initial training dataset rather small.

Although in above described embodiments, the diagnostic images have been obtained using X-ray imaging, it shall be understood that in other embodiments, the diagnostic images may likewise be retrieved by other imaging methods, such as position emission tomography, single positron emission computed tomography, magnetic resonance imaging, X-ray scanning, ultrasound imaging or the like.

Further, it shall be understood that, although in the above embodiments, the initial training dataset comprised diagnostic image data comprising corresponding vessel labeling and a plurality of diagnostic images, the initial training dataset may also be derived from a small set of three-dimensional coronary atlases containing 3D centerlines for the coronaries that may be projected onto a two-dimensional image by using the 3D geometry parameters of the X-ray system.

Further, while in the above embodiments, the analyzing has been performed on the coronary vasculature, in other embodiments, the analysis may likewise be performed on the vasculature in other parts of the human body, such as the peripheral vasculature.

It shall also be understood that, although in the above embodiments, the data has been stored in the database according to SNOMED CT, other data structures that are easy to interpret and provide unambiguous information may likewise be used.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the receiving of the diagnostic image data, the receiving of the at least one diagnostic image, the segmenting of said diagnostic image, the extracting of the centerlines, the identifying of deviations between the first and second vessel topology, et cetera performed by one or several units or devices can be performed by any other number of units or devices. These procedures in accordance with the invention can hereby be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

A method for classifying a vasculature comprising the steps of: a) training a training device with an initial model of the vasculature using diagnostic image data representing a first vessel tree, said diagnostic image data comprising a corresponding vessel labeling for at least one vessel of said first vessel tree, b) inputting at least one diagnostic image representing a second vessel tree, c) identifying at least one deviation between the first vessel tree and the second vessel tree, d) in response to the identifying, outputting an indication of said at least one deviation to a user and providing at least one labeling for said at least one deviation, and e) adjusting, based on the at least one deviation and the at least one labeling, the initial model to classify the vasculature.

By means of this method, deviations from the initial model may be resolved interactively by presenting deviations to an expert, such as a physician, who may interactively label the deviations as represented in that images and, thereby, expand the training set by the necessary knowledge about the anatomical variation between patients. This gradually yields an accurate automatic labeling of the (coronary) vasculature.

The invention claimed is:

1. A method of generating a model to classify a vasculature, the method comprising:
    obtaining a trained model of a vasculature, wherein the trained model was trained from image data that represents a plurality of first vessel trees of a plurality of vasculatures and includes labeling of at least one vessel in each of the plurality of first vessel trees;
    obtaining an image representing a second vessel tree;
    identifying a deviation between a vessel geometry in the trained model and a vessel geometry in the second vessel tree;
    providing a labeling of the deviation; and
    adjusting, based on the deviation and the labeling of the deviation, the trained model to classify the vasculature.

2. The method according to claim 1, further comprising:
    displaying an indication of the deviation to a user; and
    receiving user input providing the labeling of the deviation.

3. The method according to claim 1, wherein the adjusting of the trained model is iteratively repeating for each respective deviation of a plurality of deviations between a vessel geometry in the trained model and a vessel geometry of the respective deviation.

4. The method according to claim 1, wherein the adjusting of the trained model comprises retraining the trained model based on the plurality of first vessel trees, the labeling of at least one vessel in each of the plurality of first vessel trees, the deviation between the vessel geometry in the trained model and the vessel geometry in the second vessel tree, and the labeling of the deviation.

5. The method according to claim 1, further comprising identifying the vessel geometry of the second vessel tree in the image by:
    segmenting the image,
    identifying, based on the segmenting, centerline information for a plurality of vessels of the second vessel tree, and
    extracting the centerline information for identification of the vessel geometry of the second vessel tree.

6. The method according to claim 5, wherein the centerline information is obtained with the image representing the second vessel tree.

7. The method according to claim 1, wherein the image data comprises between 10000 and 100 images.

8. The method according to claim 1, wherein the trained model includes externally-caused variations.

9. A system for generating a model to classify a vasculature, the classification system comprising:
    a processor in communication with memory, the processor configured to:
        obtain a trained model of the vasculature, wherein the trained model was trained from image data that represents a plurality of first vessel trees of a plurality of vasculatures and includes labeling of at least one vessel in each of the plurality of first vessel trees;
        obtain an image representing a second vessel tree;
        identify a deviation between a vessel geometry in the trained model and a vessel geometry in the second vessel tree;
        provide a labeling of the deviation; and
        adjust, based on the deviation and the labeling of the deviation, the trained model to classify the vasculature.

10. The system according to claim 9, further comprising a display configured to:
    display an indication of the deviation to a user, and
    receive user input from the user indicating the labeling of the deviation.

11. The system according to claim 9, wherein the processor is further configured to generate a medical representation comprising at least the vasculature, the labeling of at least one vessel in each of the plurality of first vessel trees, and the labeling of the deviation; and transmit the medical representation to a database.

12. The system according to claim 11, wherein the database comprises an electronic medical record (EMR); and wherein the medical representation is generated according to a pre-determined format of the electronic medical record.

13. The system according to claim 9, wherein the processor is further configured to:
    segment the image,
    identify, based on the segmenting, centerline information for a plurality of vessels of the second vessel tree, and
    extract the centerline information for identification of the vessel geometry of the second vessel tree.

14. The system according to claim 9, wherein the processor is further configured to iteratively repeat adjustment of the trained model for each respective deviation of a plurality of deviations between a vessel geometry in the trained model and a vessel geometry of the respective deviation.

15. The system according to claim 9, wherein adjustment of the trained model comprises retraining the model based on the plurality of first vessel trees, the labeling of at least one vessel in each of the plurality of first vessel trees, the deviation between the vessel geometry in the trained model and the vessel geometry in the second vessel tree, and the labeling of the deviation.

16. A non-transitory computer-readable medium having stored a computer program comprising instructions which, when executed by a processor, cause the processor to:
 obtain a trained model of a vasculature, wherein the trained model was trained from image data that represents a plurality of first vessel trees of a plurality of vasculatures and includes labeling of at least one vessel in each of the plurality of first vessel trees;
 obtain an image representing a second vessel tree;
 identify a deviation between a vessel geometry in the trained model and a vessel geometry in the second vessel tree;
 provide a labeling of the deviation; and
 adjust, based on the deviation and the labeling of the deviation, the trained model to classify the vasculature.

17. The non-transitory computer-readable medium of claim 16, wherein the instruction, when executed by the processor, further cause the processor to:
 display an indication of the deviation to a user; and
 receive user input providing the labeling of the deviation.

18. The non-transitory computer-readable medium of claim 16, wherein the instruction, when executed by the processor, further cause the processor to:
 segment the image,
 identify, based on the segmenting, centerline information for a plurality of vessels of the second vessel tree, and
 extract the centerline information for identification of the vessel geometry of the second vessel tree.

19. The non-transitory computer-readable medium of claim 16, wherein the instruction, when executed by the processor, cause the processor to iteratively repeat adjustment of the trained model for each respective deviation of a plurality of deviations between a vessel geometry in the trained model and a vessel geometry of the respective deviation.

20. The non-transitory computer-readable medium of claim 16, wherein adjustment of the trained model comprises retraining the model based on the plurality of first vessel trees, the labeling of at least one vessel in each of the plurality of first vessel trees, the deviation between the vessel geometry in the model and the vessel geometry in the second vessel tree, and the labeling of the deviation.

* * * * *